United States Patent
Paik et al.

(10) Patent No.: US 7,119,213 B2
(45) Date of Patent: Oct. 10, 2006

(54) PHARMACOLOGICALLY ACTIVE ISOLATED OR PURIFIED DAUER PHEROMONE COMPOUND FOR CONTROLLING AGING AND STRESS AND METHOD FOR ISOLATING AND CHARACTERIZING THE SAME

(75) Inventors: Young Ki Paik, 102-1807, Dusan Apartment, 472, Kaebong-Dong, Kuro-Ku, Seoul (KR) 152-090; Pan Young Jeong, Seoul (KR)

(73) Assignees: Jong Mun Kim, Seoul (KR); Young Ki Paik, Seoul (KR)

( * ) Notice: Subject to any disclaimer, the term of this patent is extended or adjusted under 35 U.S.C. 154(b) by 0 days.

(21) Appl. No.: 10/490,837

(22) PCT Filed: Oct. 7, 2003

(86) PCT No.: PCT/KR03/02059

§ 371 (c)(1),
(2), (4) Date: Mar. 25, 2004

(87) PCT Pub. No.: WO2004/043944

PCT Pub. Date: May 27, 2004

(65) Prior Publication Data

US 2005/0075389 A1  Apr. 7, 2005

(30) Foreign Application Priority Data

Nov. 14, 2002  (KR) .................... 10-2002-0070591

(51) Int. Cl.
 *C07D 315/00* (2006.01)
(52) U.S. Cl. .................... 549/417; 514/460
(58) Field of Classification Search ............... 549/417; 514/460
 See application file for complete search history.

(56) References Cited

OTHER PUBLICATIONS

Chem. Abs vol. 134 No. 160429(2000).*
Chem. Abs. vol. 132 No. 163700(2000).*
Chem. Abs. vol. 127 No. 642760(1997).*
Curran Angew. Chem. Int. Ed. vol. 37 pp. 1175-1190, 1194-1196(1998).*
Pan-Young Jeong, et al; "Chemical structure and biological activity of the *Caenorhabditis elegans* dauer-inducing pheromone"; letters to nature, vol. 433, Feb. 3, 2005, Nature Publishing Group; pp. 541-545.
Golden, James W., et al; "A pheromone-induced developmental switch in *Caenorhabdits elegans*: temperature-sensitive mutants reveal a wild-type temperature-dependent process"; Proc. Natl. Acad. Sci., United States of America, vol. 81, Feb. 1984, pp. 819-923.

(Continued)

Primary Examiner—Thomas McKenzie
Assistant Examiner—Raymond Covington
(74) Attorney, Agent, or Firm—Norris McLaughlin & Marcus PA (57) ABSTRACT

The present invention discloses a method for effectively isolating and purifying a physiological active dauer pheromone compound having the following structural formula I related to aging and stress of *C. elegans*, and determination of the structure of such material. First, ethanol extract is prepared by completely concentrating a liquid medium with ethanol after culturing *C. elegans* on a S. basal liquid medium, and then this ethanol fraction is further extracted with ethyl acetate. Then, impurities are removed from ethyl acetate extract by a silica-gel adsorption chromatography and a pheromone extract is isolated and purified by amine column chromatographic procedures using various solvents as eluent. Finally, a pheromone compound having structural formula I is completely isolated and characterized by size-exclusion HPLC.

9 Claims, 8 Drawing Sheets

OTHER PUBLICATIONS

Ogg, Scott, et al; "The fork head transcription factor DAF-16 transduces insulin-like metabolic and longevity signals in *C. elegans*"; Nature, vol. 389, Oct. 30, 1997; pp. 994-999.

Golden, James W. et al; "A pheromone influences larval development in the nematode *Caenorhabditis elegans*"; Science, vol. 218, Nov. 5, 1982; pp. 578-580.

Tissenbaum, Heidi A., et al; "A common muscarinic pathway for diapause recovery in the distantly related nematode species *Caenorhabditis elegans* and *Ancylostoma caninum*"; PNAS, vol. 97, No. 1, Jan. 4, 2000; pp. 460-465.

Vowels, Jennifer J. et al; "Multiple chemosensory defects in *daf*-11 and *daf*-21 mutants of *Caenorhabditis elegans*"; Genetics 138, Oct. 1994, pp. 303-316.

Zwaal, Richard R.; "Two neuronal G proteins are involved in chemosensation of the *Caenorhabditis elegans* dauer-inducing pheromone"; Genetics 145; Mar. 1997, pp. 715-727.

Inoue, Takao et al.; "Suppressors of transforming growth factor-β pathway mutants in the *Caenorhabditis elegans* dauer formation pathway"; Genetics 156; Nov. 2000; pp. 1035-1046.

Ailion, Michael et al; "Dauer formation induced by high temperatures in *Caenorhabditis elegans*"; Genetics 156; Nov. 2000; pp. 1047-1067.

* cited by examiner

Dauer formation

PHARMACOLOGICALLY ACTIVE ISOLATED OR PURIFIED DAUER PHEROMONE COMPOUND FOR CONTROLLING AGING AND STRESS AND METHOD FOR ISOLATING AND CHARACTERIZING THE SAME

TECHNICAL FIELD

The present invention relates to a novel dauer pheromone and its structural determination, more specifically, to a dauer pheromone, which can induce *C. elegans* into a dauer larva stage. The present invention also relates to a novel method for efficiently isolating and purifying a physiologically active dauer pheromone, and determination of the structure of such material.

BACKGROUND ART

Pheromones are defined as substances that are used for communication between individuals of the same species. Pheromones are usually obtained in the form of mixtures through multiple separation steps including organic solvent extraction and liquid column chromatography.

In early 1980s, it was reported that *C. elegans* can secret a type of pheromone, termed 'dauer pheromone', a constitutively secreted substance serving as an indicator of population density (Golden and Riddle 1982, Golden and Riddle 1984a, Golden and Riddle 1984c), which can induce *C. elegans* into dauer arrest phase when they are faced with adverse environmental conditions such as heat, lack of food, and crowdedness. Although its presence has been known for more than two decades, its structure, molecular weight and physical properties are not known yet (Riddle, D. L., Science, 218: 578–580, 1982).

According to the previous studies, pheromone secreted from *C. elegans* exists in extremely low concentration. Because of its potential in control of aging and stress in *C. elegans*, the dauer pheromone has been studied extensively. However, until now, because it was not available in a single molecule, most investigators have used the crude extracts of *C. elegans* that are believed to contain a dauer pheromone and other compounds as well.

Therefore, it is necessary to isolate a pure dauer pheromone from the extracts and characterize its structure for the studies of aging, stress and other cellular function of *C. elegans*. The dauer pheromone is likely to be detected by as yet unidentified pheromone receptor that couples to a cyclic GMP signaling pathway that includes daf-11 (Birnby et al. 2000). It has been known that the dauer pheromone of *C. elegans* is very stable and hydrophobic, and has chromatographic properties similar to those of hydroxylated fatty acids and bile acids.

In this article, we describe purification, identification, and molecular characterization of *C. elegans*-specific dauer pheromone.

DISCLOSURE OF THE INVENTION

The present inventors have conducted an extensive research for many years in order to isolate a novel class of dauer pheromone, which can be widely used for studies on aging, stress, signal transduction and various biological problems. As a result, the inventors have discovered that an extract obtained from *C. elegans*, which has been studied as a good animal model for various diseases, contains a novel dauer pheromone and purification of this extract by stepwise separation procedures results in pure dauer pheromone. Based on this finding, it is possible to provide a novel dauer pheromone.

It is therefore an object of the present invention to provide a novel dauer pheromone, which comprises extraction of *C. elegans* with one or more solvents selected from the group consisting of water, alcohols, and ethyl acetate and chromatographic separation with various solvents as eluent.

Further object of the present invention is to provide 6-(3,5-dihydroxy-6-methyl-tetrahydro-pyran-2-yloxy)-heptanoic acid or the salts thereof, which can be represented by formula I as set forth below.

Structural Formula I

Still another object of the present invention is to provide to a composition for dauer inducing activity, which comprises 6-(3,5-dihydroxy-6-methyl-tetrahydro-pyran-2-yloxy)-heptanoic acid or the salts thereof, and a pharmaceutically acceptable carrier.

Still another object of the present invention is to provide a pharmaceutical composition for inducing dauer state of *C. elegans* or controlling aging state of animals.

Still another object of the present invention is to provide a method for isolating and purifying a dauer pheromone using the several chromatographic procedures.

The method includes the steps of 1) ethanol extraction of *C. elegans* that have been grown on a S. basal liquid medium by feeding *Escherichia coli*;

2) ethyl acetate extraction of ethanol extracts as prepared in the step 1;

3) efficient removal of impurities from ethyl acetate fractions by a silica-gel adsorption chromatography;

4) separation and purification of a dauer pheromone by high performance chromatography (HPLC) using various amine columns.

Further objects and advantages of the invention will become apparent through the remainder of the specification.

The foregoing has outlined some of the more pertinent objects of the present invention. These objects should be constructed to be merely illustrative of some of the more pertinent features and applications of the invention. Many other beneficial results can be obtained by applying the disclosed invention in a different manner or modifying the invention within the scope of the disclosure. Accordingly, other objects and a more through understanding of the invention may be given by referring to the detailed description of the preferred embodiment in addition to the scope of the invention defined by the claims.

BEST MODE FOR CARRYING THE INVENTION

Herein below, the application will be illustrated in more detail.

An isolated pheromone for the purpose of the present invention is 6-(3,5-dihydroxy-6-methyl-tetrahydro-pyran-2-yloxy)-heptanoic acid or the salts thereof which can be represented by the formula I below. The compound of formula I markedly induce the worm into dauer phase.

Structural Formula I

The compound of formula I may be formulated into a pharmaceutical composition with pharmaceutically acceptable recipients or carriers. Especially, the composition can be desirably used as various experimental reagents for controlling dauer phase of animals and for studying the mechanisms of aging, stress, signal transduction, neurological disease and metabolic diseases.

The novel pheromone compound or its salt, which is a physiologically active material which in fact is able to induce C. elegans enter into the dauer larva stage when this pure pheromone is added onto the media. This is found to be a novel pheromone compound, which has the above structural formula I, and its chemical formula is 6-(3,5-dihydroxy-6-methyl-tetrahydro-pyran-2-yloxy)-heptanoic acid.

The first goal of the present invention is to prepare highly purified single molecule of dauer pheromone of C. elegans in large quantities, which can be used for the studies of aging, signal transduction, metabolic regulation and stress. The second goal is to characterize its chemical structure and verify whether the isolated pure dauer pheromone is novel and contains biologically functional dauer inducing compound using various analytical techniques and biological assays.

The pheromone compound or its salt, which was isolated and characterized through the present invention is a compound secreted from C. elegans, exhibits dauer pheromone activity.

A pheromone activity fraction that is currently being used for studying on aging, signal transduction and stress by many researchers is a crude extract which is prepared by ethanol extraction of cultured C. elegans. Therefore, with availability of the pure dauer pheromone, it is now possible to study on aging, signal transduction and stress to which a dauer pheromone is involved.

Preferred embodiments of the present invention will be described more in detail in conjunction with the accompanying tables and drawings.

Although preferred embodiments of the present invention have been described in detail hereinabove, it should be clearly understood that many variations and/or modifications of the basic inventive concepts herein taught, which may applied to those skilled in the present art will still fall within the spirit and scope of the present invention, as defined in the appended claims.

Embodiment

After C. elegans are cultured on a S. basal liquid medium for 5 days at a temperature of 20° C. by feeding Escherichia coli (OP50), they are further cultured for 10 more days by additional feeding.

A centrifugal separation is carried out to obtain a broth after over the 70% of the worms entered into the dauer larva stage. The liquid phase of culture media was obtained by a removal of the worms and Escherichia coli through membrane filtration using a membrane filter of 0.45 μm.

The pure medium in a powder state can be obtained by completely dehydrating the media by vacuum evaporator.

Ethanol is added to the powder form of media and extraction of this solution with ethanol is performed. This process is repeated 3 times.

To examine whether this ethanol extract (A) can induce dauer larva phase, dauer test is performed on the worms that had been grown in the S medium.

Table 1 shows a dauer inducing activity of A. Once A shows the dauer inducing activity, it is further extracted with ethyl acetate. Briefly, the dried A was dissolved in double distilled water and extracted with the equal volume of ethyl acetate. This extraction procedure was repeated 5 times.

Table 2 shows an assay result of ethyl acetate extract (B) on the dauer inducing activity against C. elegans. After confirming the dauer inducing activity of B, extracts obtained by the above-described process are loaded onto a silica-gel absorption column which has been equilibrated with hexane: ethyl acetate: methanol=7:7:1. An active form of dauer pheromone (C) that were adsorbed onto the column was eluted with methanol.

Table 3 summarizes shows the result of dauer inducing assay with a fraction (C) obtained from a silica-gel column. To further purify C, HPLC separation is carried out using amine column. Briefly, the fraction C is dissolved in methanol and diluted with double distilled water (MeOH: ddH$_2$O=1:1). This solution containing C is loaded onto the amine column, which is equilibrated with isopropanol solution (isopropanol: water=1:1). A dauer pheromone fraction bound to the column (Fraction D) was eluted with a gradient solution of the same solvent. Table 4 shows a pattern of elution profile with time obtained from an amine column chromatography.

Table 5 outlines the result of dauer inducing assay using the active fractions D from the amine column chromatography. Finally, a dauer pheromone (E) is completely isolated and purified refined by size exclusion column chromatography using methanol as an eluent solution.

Table 6 summarizes the assay results of a dauer inducing activity of the purified dauer pheromone. The pure dauer pheromone characterized by the above described procedures is defined as the structural formula I, and its chemical formula is 6-(3,5-dihydroxy-6-methyl-tetrahydro-pyran-2-yloxy)-heptanoic acid or its sodium salt.

The 6-(3,5-dihydroxy-6-methyl-tetrahydro-pyran-2-yloxy)-heptanoic acid may react with a base to make its salt form. The base can be one of alkaline or alkaline earth metal salt that is pharmaceutically applicable. For example, sodium, potassium, magnesium, or calcium can be used as the base.

The molecular weight of the pure dauer pheromone, 6-(3,5-dihydroxy-6-methyl-tetrahydro-pyran-2-yloxy)-heptanoic acid is 276 Dalton, and a molecular formula thereof is $C_{13}H_{24}O_6$. However, the molecular weight of its isolated form turns out to be 299 Dalton because 1 molecule of sodium is bound to it by non-covalent bond in order to exhibit a biological activity.

The difference in molecular weight between the pure form and the isolated one is found by analyzing quadruple tandem mess spectrometer, from which 1 molecule of sodium is non-covalently bounded to the acidic form. In addition, the purified pheromone compound, 6-(3,5-dihydroxy-6-methyl-tetrahydro-pyran-2-yloxy)-heptanoic acid, can also become an ammonium salt form, which leads to confirm its molecular weight 276 Dalton.

Figure 1:
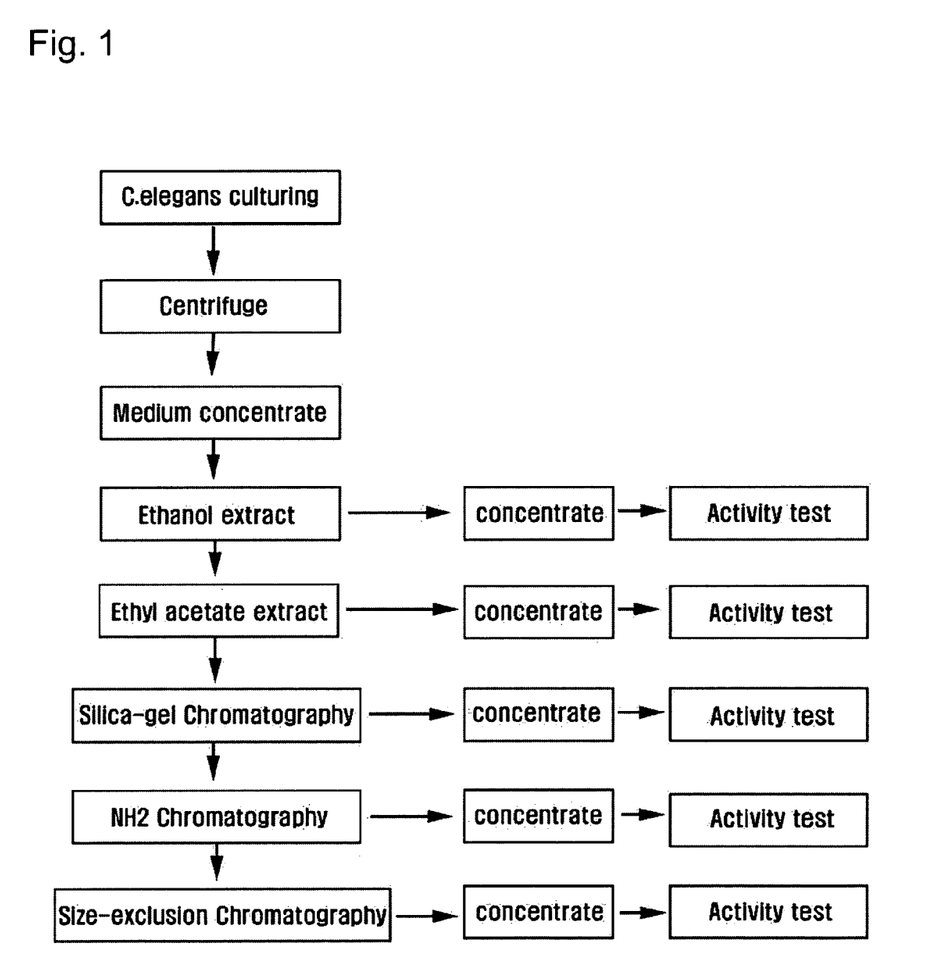
FIG. 1 is a schematic view, which illustrates a stepwise method for isolating and purifying an inventive pheromone compound from *C. elegans*.
Figure 2:
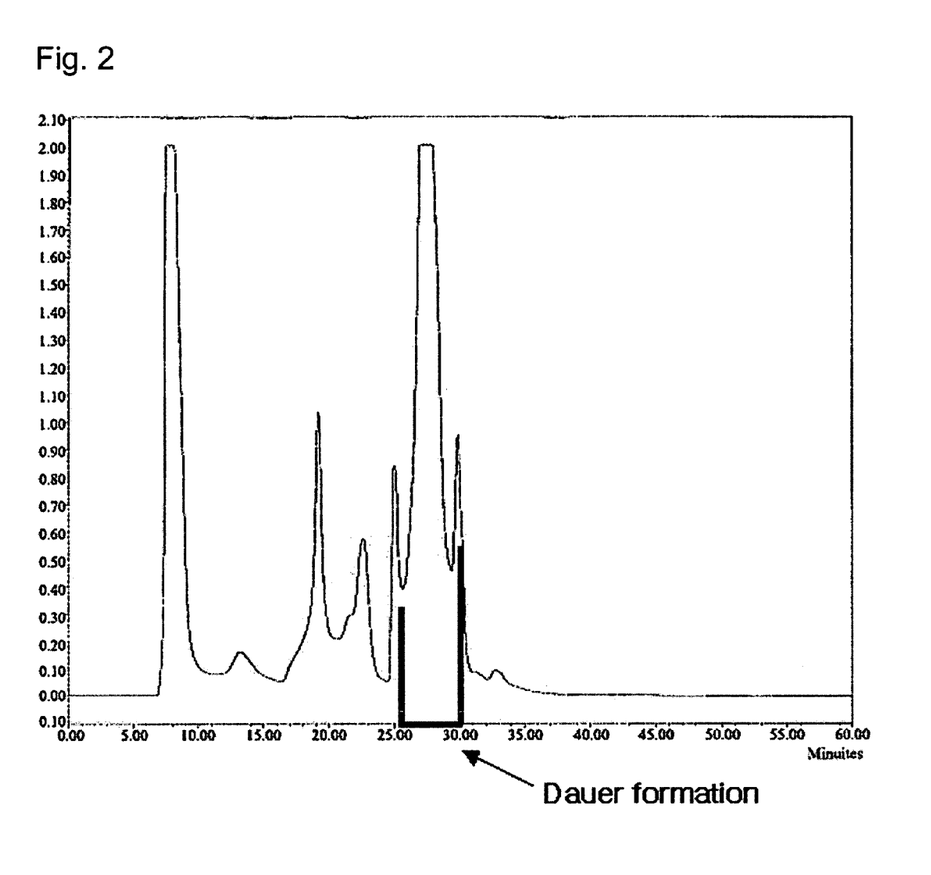
FIG. 2 is a typical chromatogram, which illustrates enrichment of active fractions by HPLC with amine columns employing gradient elution with distilled water and isopropanol as a solvent.
Figure 3:
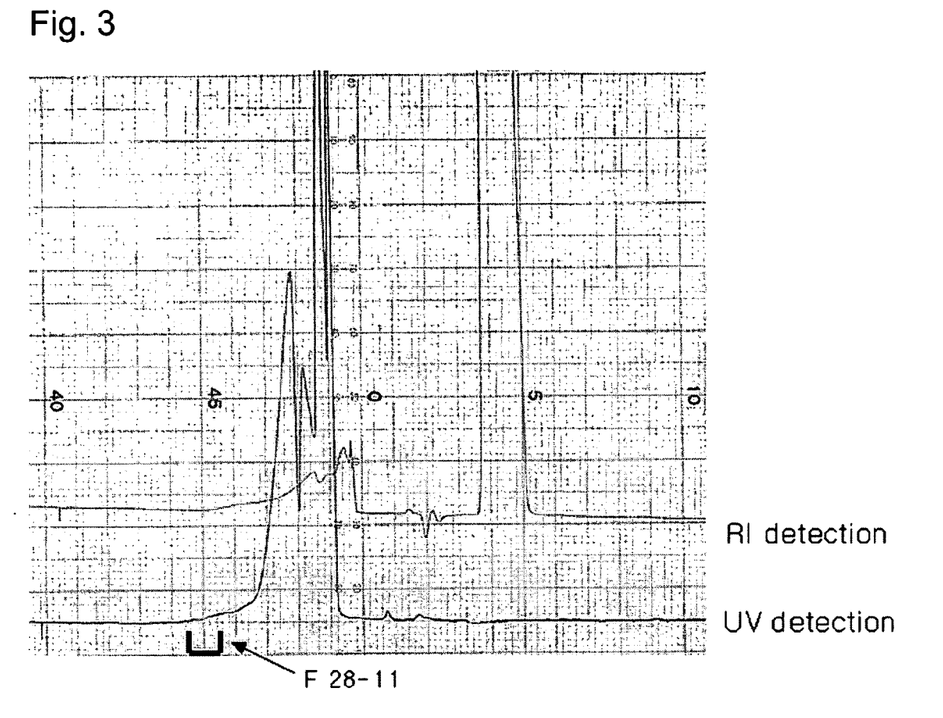
FIG. 3 represents a chromatogram of HPLC separated by molecular weight (W251), which was run on the isocratic elution condition using methanol as a solvent.
Figure 4:
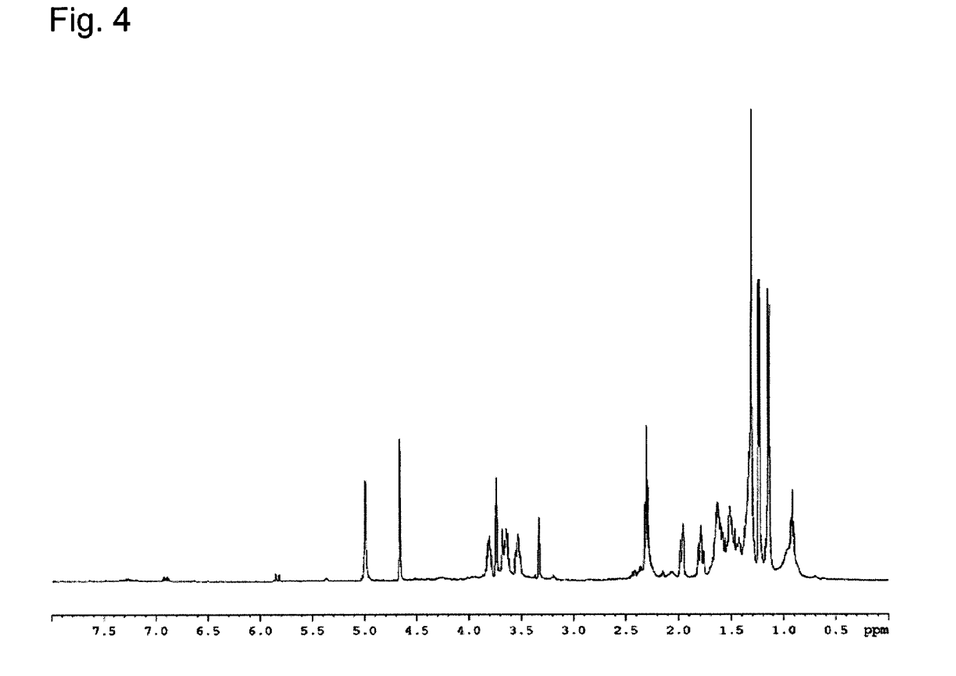
FIG. 4 is a graph of a hydrogen nuclear magnetic resonance spectrum (1H-NMR) measured by using deuterio methanol (CD$_3$OD) as a solvent.
Figure 5:
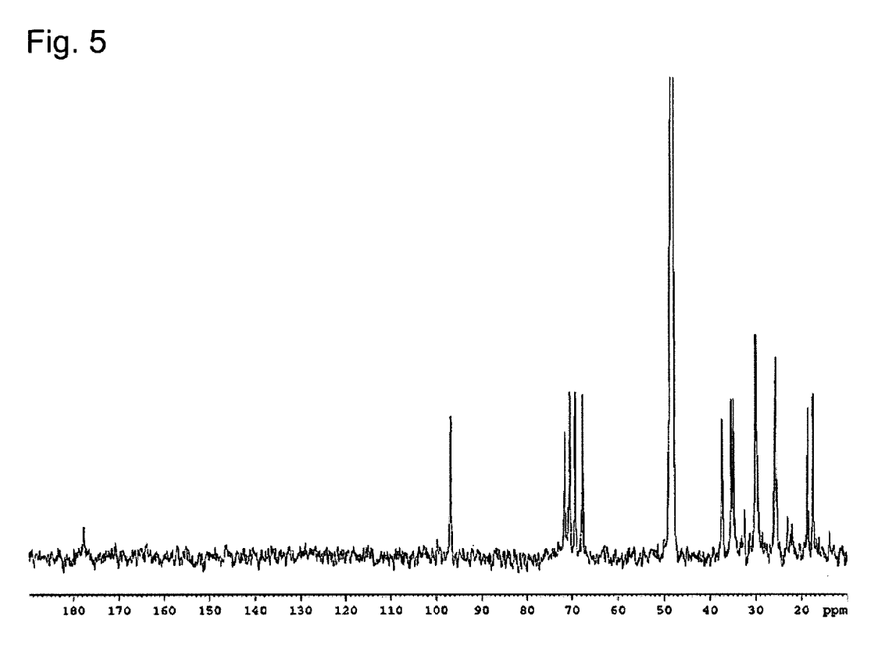
FIG. 5 is a graph of a carbon nuclear magnetic resonance spectrum (13C-NMR) measured by using deuterio methanol (CD$_3$OD) as a solvent.
Figure 6:
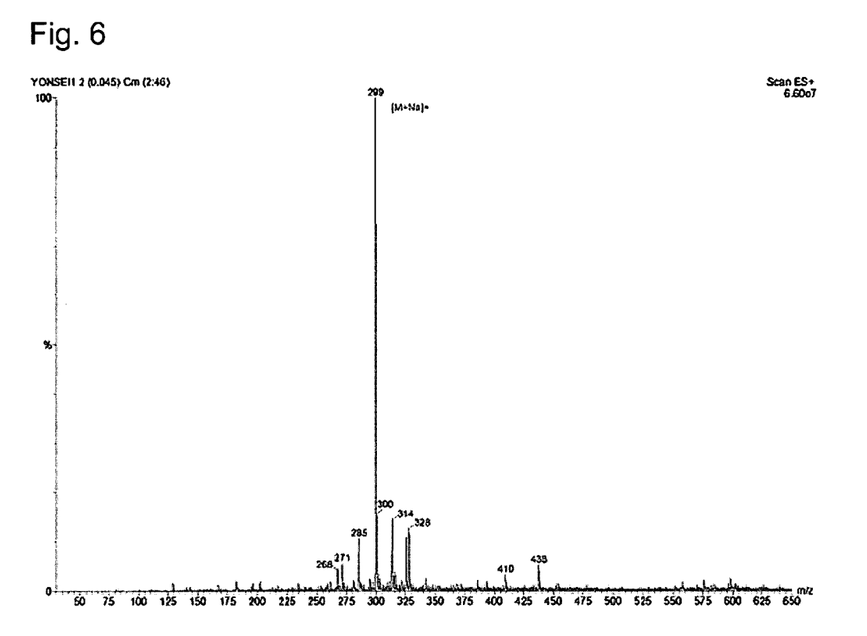
FIG. 6 is a graph illustrating molecular mass spectrum measured in a positive mode using a quadruple type mass spectrometer.
Figure 7:
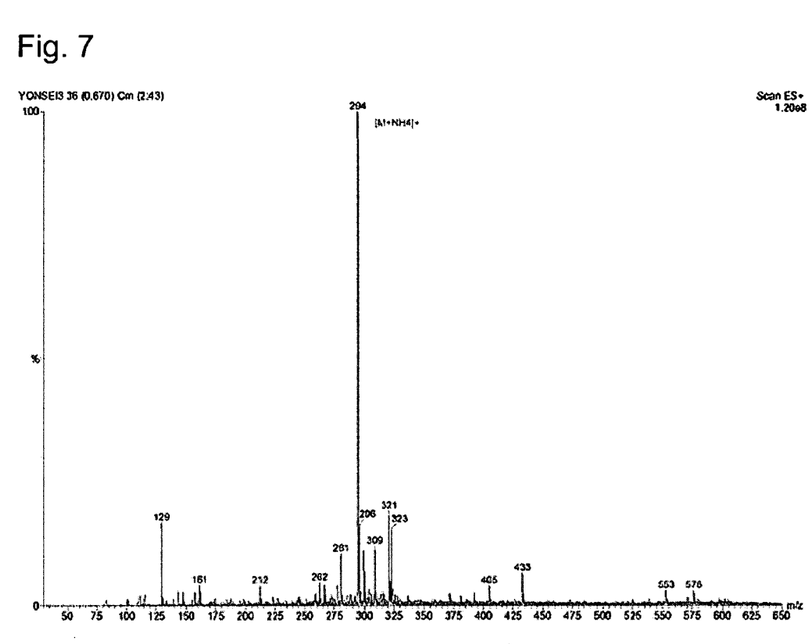
FIG. 7 is a graph illustrating a result of a mass spectrum of pheromone measured in the presence of sodium acetate during the measurement process in a positive mode using a quadruple type mass spectrometer.
Figure 8:
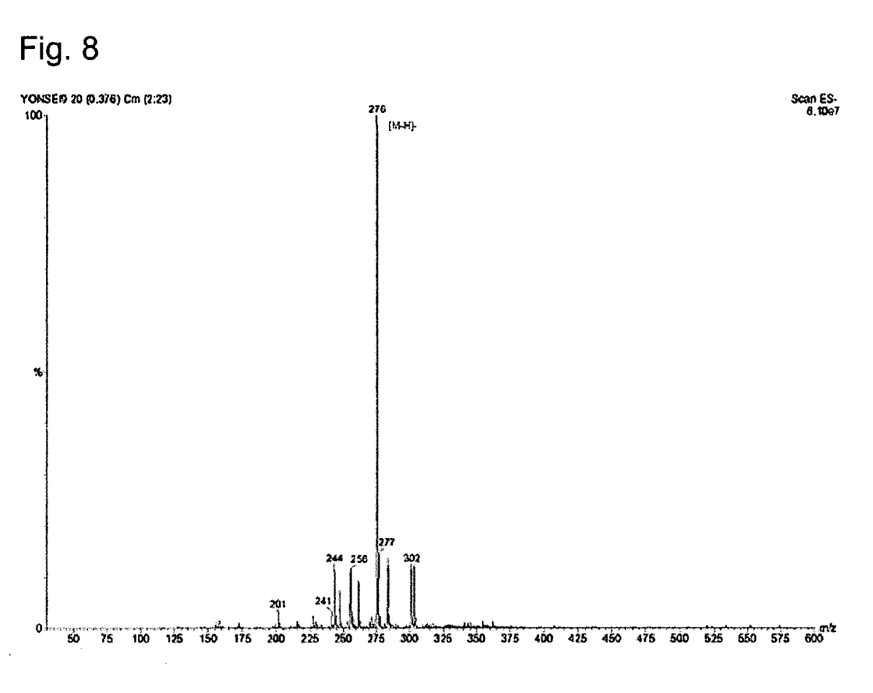
FIG. 8 is a graph illustrating a result of a mass measured in a negative mode using a quadruple type mass spectrometer.

To determine the chemical structure of the inventive pheromone having the formula I, a hydrogen nuclear magnetic resonance spectrum (1H-NMR) is analyzed using deuterio methanol ($CD_3OD$) as a solvent. And a carbon nuclear magnetic resonance spectrum (13C-NMR) can also be analyzed using deuterio methanol ($CD_3OD$) as a solvent.

A chemical shift is set with a ppm unit. The definite 1H- and 13C-NMR chemical shift are obtained by using two-dimensional NMR technique such as 1H-1H DQF-COSY spectrums, 13C-1H HMBC. The results are shown in Table 7. That is, spectrum analysis result of 1H NMR (MHz), 13C NMR (MHz) of a dauer pheromone confirmed that its molecular formula is 6-(3,5-dihydroxy-6-methyl-tetrahydro-pyran-2-yloxy)-heptanoic acid.

INDUSTRIAL APPLICABILITY

As described above, from the present invention, we are able to obtain a novel dauer pheromone from *C. elegans* and to determine its chemical structure as 6-(3,5-dihydroxy-6-methyl-tetrahydro-pyran-2-yloxy)-heptanoic acid, which can exist as its various salt forms. Now our invention can lead to research on the aging, signal transduction, stress, metabolism, obesity, and neurological disorders. This invention further leads us to the development of the pharmacologically useful drug candidate molecule for broad types of many diseases.

TABLE 1

| | Dauer inducing activity of ethanol extract |
|---|---|
| Formation of dauer larva stage (%) | 100 |
| Population in dauer larva stage | 173 |

TABLE 2

| | Dauer inducing activity of ethyl acetate fraction |
|---|---|
| Formation of dauer larva stage (%) | 100 |
| Population in dauer larva stage | 194 |

TABLE 3

| | Dauer inducing activity of the silica-gel bound fraction |
|---|---|
| Formation of dauer larva stage (%) | 100 |
| Population in dauer larva stage | 110 |

TABLE 4

| Time (Minute) | Flow rate (ml/min) | Isopropanol (%) | Distilled water (%) |
|---|---|---|---|
| 0 | 2 | 100 | 0 |
| 5 | 2 | 100 | 0 |
| 35 | 2 | 0 | 100 |
| 45 | 2 | 0 | 100 |

TABLE 5

| | Dauer inducing activity of the amine column fractions |
|---|---|
| Formation of dauer larva stage (%) | 100 |
| Population in dauer larva stage | 92 |

TABLE 6

| | Dauer inducing activity of W251 column fraction (purified form) |
|---|---|
| Formation of dauer larva stage (%) | 100 |
| Population in dauer larva stage | 62 |

TABLE 7

| | Atom | DEPT | $^1H$ (ppm) | $^{18}C$ (ppm) | DQF-COSY | HMBC (H->C) |
|---|---|---|---|---|---|---|
| Pheromone | 1 | COOH | | 177.299 | | C-2,3 |
| | 2 | $CH_2$ | 2.299 | 34.583 | H-3 | C-3 |
| | 3 | $CH_2$ | 1.644 | 25.415 | H-2 | C-2,4,5,6,7 |
| | 4 | $CH_2$ | 1.469 | 29.955 | H-3,5 | C-2,3,5 |
| | 5 | $CH_2$ | 1.500 1.584 | 37.121 | H-6 | C-3,4,6,7 |
| | 6 | CH | 3.808 | 71.331 | H-5,7 | C-5,7 |
| | 7 | $CH_8$ | 1.145 | 18.327 | H-6 | C-5 |
| | 2' | CH | 4.663 | 96.559 | H-3' | C-4' |
| | 3' | CH | 3.734 | 69.027 | H-2',4' | C-2',4' |
| | 4' | $CH_2$ | 1.791 1.974 | 34.934 | H-3',5' | C-2',5',6' |
| | 5' | CH | 3.548 | 67.445 | H-4',6' | C-3',4',6',7' |
| | 6' | CH | 3.644 | 70.218 | H-5',7' | C-4',5',7' |
| | 7' | $CH_8$ | 1.236 | 17.175 | H-6' | C-5',6' |

The invention claimed is:

1. An isolated or purified dauer pheromone compound or its salts, represented by the following structural formula I.

Structural Formula I

2. A dauer pheromone compound or its salts of claim 1 wherein the salt is 6-(3,5-dihydroxy-6-methyl-tetrahydro-pyran-2-yloxy)-heptanoic acid sodium salt.

3. A salt formed as the reaction product of 6-(3,5-dihydroxy-6-methyl-tetrahydro-pyran-2-yloxy)-heptanoic acid and an alkali or alkali earth metal salt base.

4. A composition for dauer inducing activity comprising a therapeutically effective amount of 6-(3,5-dihydroxy-6-methyl-tetrahydro-pyran-2-yloxy)-heptanoic acid or the salts thereof, and a pharmaceutically acceptable carrier.

5. A pharmaceutical composition of claim 4 wherein the composition induces dauer state of *C. elegans* or controls aging state of animals.

6. A method for isolating and characterizing a dauer pheromone compound or its salts, represented by the following structural formula I, comprising the steps of:
   extracting total culture broth of *C. elegans* with ethanol (Fraction A),
   extracting the Fraction A with ethyl acetate to prepare Fraction B after dissolving the ethanol extract in water;
   removing impurities from the Fraction B by a silica-gel adsorption chromatography (Fraction C);
   isolating and purifying the Fraction C by HPLC using amine column to prepare Fraction D; and
   completely purifying the Fraction D to prepare a pure dauer pheromone compound by additional HPLC with molecular size exclusion column Structural Formula I 7. A method of claim 6 wherein the step of removing comprises the steps of removing impurities by running on the silica-gel adsorption column chromatography that is equilibrated with hexane:ethyl acetate:methanol=7:7:1 and then eluting a partially purified pheromone fraction by the silica-gel adsorption column chromatography that is eluted with methanol.

8. A method of claim 7 wherein a pheromone fraction is obtained by isolating and purifying the partially purified pheromone fraction by a HPLC with an amine column, by a gradient elution method with a solution composition of isopropanol and distilled water.

9. A method of claim 8 wherein a biologically active pheromone compound is isolated by a HPLC with a column (W251) isolating the pheromone fraction by a molecular weight through isocratic elution with a methanol solvent.

* * * * *